United States Patent
Ence

(10) Patent No.: US 6,512,583 B1
(45) Date of Patent: *Jan. 28, 2003

(54) APPARATUS AND METHOD FOR THE DIMENSIONAL MEASUREMENT OF AIRBORNE FIBERS

(75) Inventor: Brian M. Ence, Lansdale, PA (US)

(73) Assignee: Certainteed Corporation, Valley Forge, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/743,555

(22) Filed: Nov. 4, 1996

(51) Int. Cl.[7] ................................................ G01N 21/00
(52) U.S. Cl. ........................................ 356/338; 356/343
(58) Field of Search ................................ 356/335–343; 250/564, 573–577

(56) References Cited

U.S. PATENT DOCUMENTS

| | | | | |
|---|---|---|---|---|
| 3,692,412 A | * | 9/1972 | Chubb | 356/338 |
| 3,740,148 A | * | 6/1973 | Moroz et al. | 356/336 |
| 4,249,244 A | | 2/1981 | Shofner et al. | |
| 4,473,296 A | * | 9/1984 | Shofner et al. | 356/338 |
| 4,595,291 A | * | 6/1986 | Tatsuno | 356/336 |
| 4,596,036 A | * | 6/1986 | Norgren et al. | 356/336 |
| 4,737,648 A | * | 4/1988 | Smith et al. | 356/343 |
| 4,839,529 A | | 6/1989 | Fruengel | 356/339 |
| 4,916,325 A | | 4/1990 | Rood et al. | 250/573 |
| 4,940,327 A | | 7/1990 | Lilienfeld | 356/338 |
| 5,001,463 A | | 3/1991 | Hamburger | 356/438 |
| 5,303,029 A | | 4/1994 | Sioma et al. | 356/339 |
| 5,859,705 A | * | 1/1999 | Benedetto et al. | 356/336 |
| 6,122,054 A | * | 9/2000 | Ence | 356/338 |

OTHER PUBLICATIONS

*FM–7400 Real–Time Laser Fiber Monitor*, Monitoring Instruments for the Environment, Inc., 3/91, 4 pages.

* cited by examiner

Primary Examiner—Zandra Smith
(74) Attorney, Agent, or Firm—Duane Morris LLP

(57) ABSTRACT

Apparatus and method are provided for measuring a dimension of an airborne fiber. The apparatus includes a flow channel for providing a laminar flow to at least a portion of the fibers in air sample and a light source for projecting a light beam along a selected beam path to impinge upon a first fiber in the sample to create scattered light. A portion of the scattered light is measured by a light detector to produce an electrical output which is related to the fiber's dimension.

28 Claims, 4 Drawing Sheets

APPARATUS AND METHOD FOR THE DIMENSIONAL MEASUREMENT OF AIRBORNE FIBERS

CROSS REFERENCE TO RELATED APPLICATION

This application is related to co-pending non-provisional U.S. patent application Ser. No. 08/743,554, entitled "Device For Measuring The Concentration Of Airborne Fibers", filed Nov. 4, 1996, which is assigned to the same assignee hereof, and is incorporated herein by reference.

FIELD OF THE INVENTION

This invention relates to devices for measuring the dimension of airborne fibers and more particularly, to non-contact optical devices for measuring the diameter and length of flowing fibers.

BACKGROUND OF THE INVENTION

Existing airborne fiber dimension measuring devices typically require that the fibers in the sampled air be separated, aligned, and analyzed individually. Furthermore, some devices require multiple sensors which determine airborne fiber dimensions by analyzing the residual amount of direct light from collimated light beams that have been attenuated or otherwise disturbed by a passing fiber. The accuracy of devices requiring multiple sensors can be adversely affected by alignment errors, calibration drift, component degradation and the like.

Two examples of existing methods and apparatus for the measurement of entities in fiber samples include, for example, U.S. Pat. No. 5,430,301 to Shofner, et al. (1995), entitled "Apparatus and Methods for Measurement and Classification of Generalized Neplike Entities in Fiber Samples" (Shofner I); and U.S. Pat. No. 5,270,787 to Shofner, et al. (1993) entitled, "Electro-Optical Methods and Apparatus for High Speed, Multivariate Measurement of Individual Entities in Fiber or Other Samples" (Shofner II). See also MIE Fiber Monitor Model FM-7400 User's Manualby MIE, Inc., Billerica, Mass.

In Shofner I, multiple sensors are provided for measuring fiber characteristics in a sample of textile material, including small clumps or entanglements of fiber known as neps. Although this apparatus and method may be suitable for determining the characteristics of neps from textile samples, it is generally unsuitable for characterizing airborne fibers, such as glass fibers, having a diameter of less than about 10 microns.

Similarly, the device in Shofner II employs multiple sensors to directly measure the amount of light remaining from a collimated light beam which has been at least partially extinguished by the passage of a fiber between the source of the collimated light beam and the sensor. Shofner II analyzes ribbon-shaped cotton fibers with a typical width of approximately 20 microns. In addition, Shofner II analyzes the diffraction pattern that results from a cotton fiber passing through the sensing zone. This apparatus and device is also unsuitable for certain other fibers, particularly those of narrow diameter, such as glass fibers having a diameter of less than about 5–10 microns due to its non-monotonic response to fiber diameter.

What is therefore needed is an airborne fiber dimension measuring device that can accurately characterize the dimensions of small-diameter fibers.

SUMMARY OF THE INVENTION

This invention provides devices and methods for determining the dimension of airborne fibers. The device includes flow means for providing a laminar flow to at least a portion of a group of fibers in a air sample. These aligned fibers are then illuminated with a light source to create scattered light. A light detector is then used for sensing a portion of the scattered light and for generating an output from which a dimension of a first of these fibers can be provided.

This invention takes advantage of the characteristics of scattered light to produce very accurate measurements of fiber dimensions, such as diameter and length. In preferred embodiments, scattered light is collected from a slotted opening at an angle of about 60° to about 120° relative to the direction of the light source to produce an approximate monotonic voltage amplitude range, indicative of a fiber diameter.

This invention also provides a method for measuring a dimension of an airborne fiber. The method includes providing a fiber-containing air sample having a laminar flow. This air sample is thereafter contacted by a light beam to produce scattered light. The scattered light is sensed and an electrical output is produced which is representative of a sensed portion of the scattered light. This electrical output is then processed to produce a perceptible indication of a dimension of at least a first fiber in said sample.

BRIEF DESCRIPTION OF THE DRAWINGS

The accompanying drawings, referenced to herein and constituting a part hereof, illustrate preferred embodiments of the device of the present invention and, together with the description, serve to explain the principles of the invention.

DETAILED DESCRIPTION OF THE INVENTION

Figure 1:
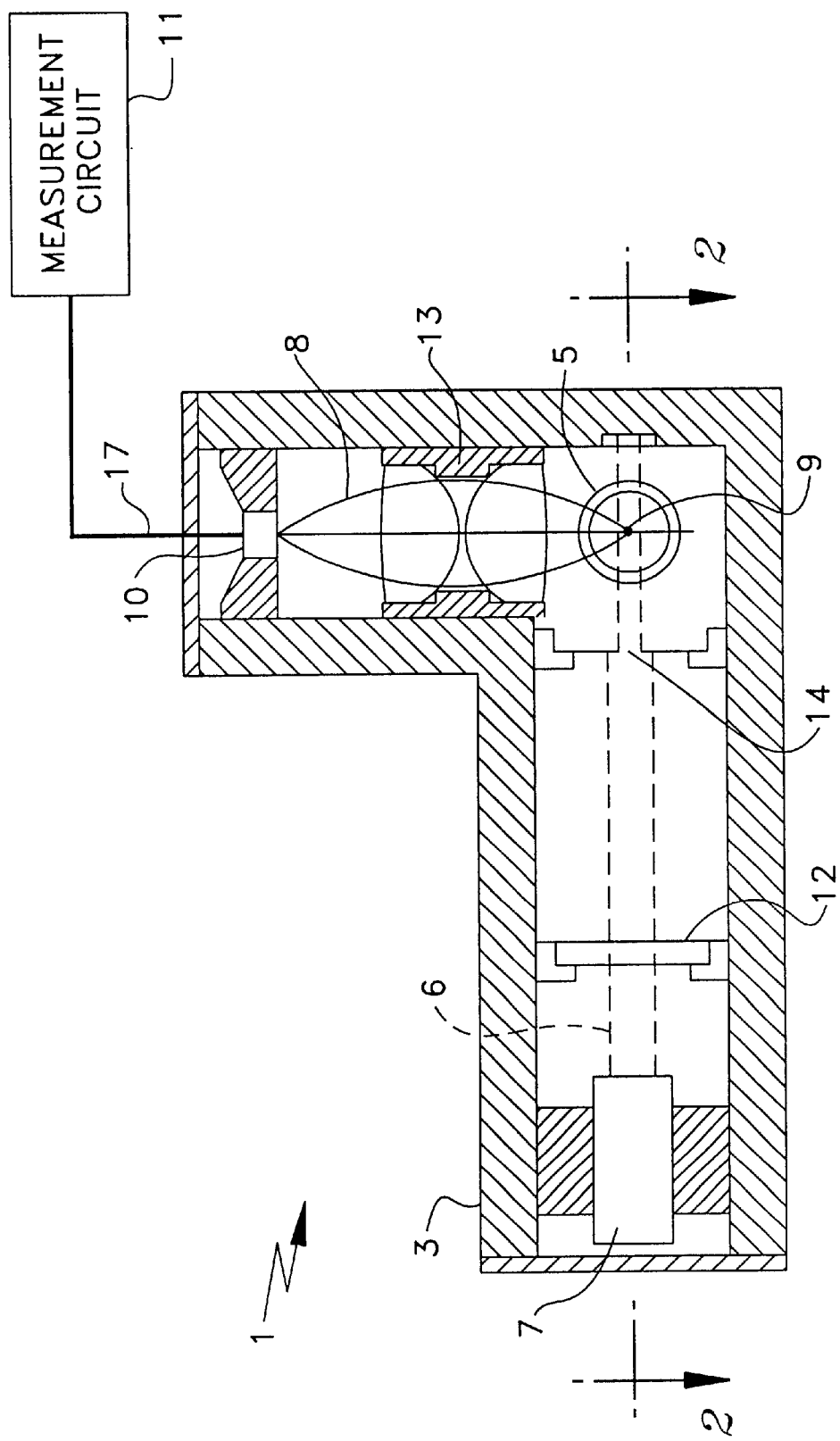
FIG. 1 is a front cross-sectional illustration of one embodiment of the present invention.
Figure 2:
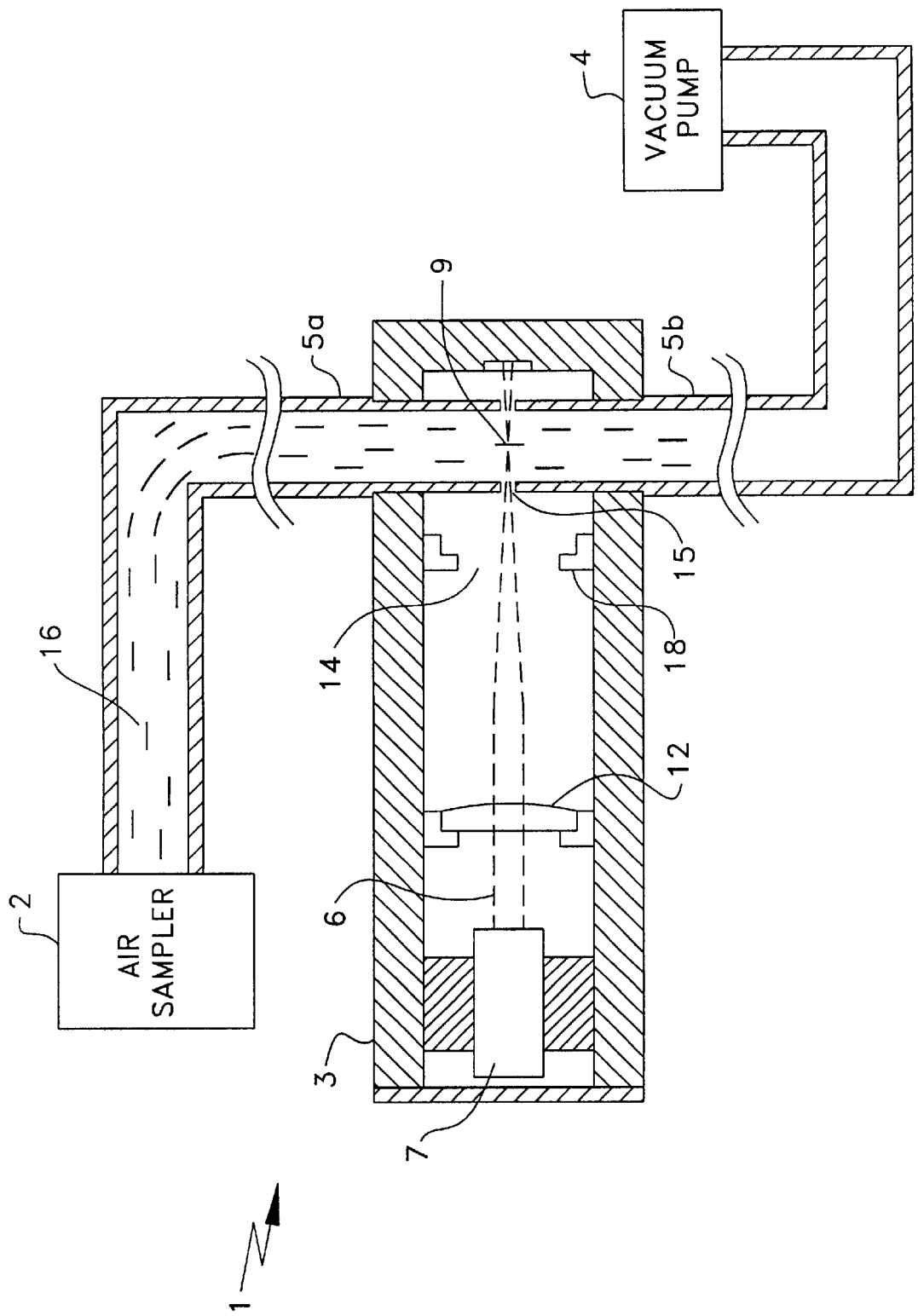
FIG. 2 is a top cross-sectional illustration of the embodiment presented in FIG. 1.

FIG. 1 illustrates a cross-sectional view of one embodiment of device 1, sectioned in a plane generally perpendicular to the airflow. FIG. 2 illustrates a top view of the embodiment of FIG. 1, along the plane indicated by line 2—2. Referring to FIGS. 1 and 2, device 1 can include sensor 3; alone, or with air sampler 2, sensor 3, vacuum pump 4, and flow tubes 5a, 5b in combination. Air sampler 2 can be used to prefilter, or condition, the fiber-laden air 16, or may be merely a sampling conduit. Sensor 3 is preferred to be an electro-optical sensor which provides a collimated light beam 6 using light source 7. Light source 7 is preferred to be a laser diode. A suitable laser diode can be, for example, a model LPM03(670-5) laser diode from Power Technology, Inc., Little Rock, Ark.

When collimated light beam 6 strikes airborne fiber 9, for example a cylindrical glass fiber, scattered light 8 is produced. It may be desirable to provide a light beam 6 with a preselected cross-section along the path of beam 6, for example, an narrow elliptical cross-section. A portion of scattered light 8 is detected by light sensor 10, which can be a photodetector. A suitable photodetector is, for example, Devar Model 509-10, Bridgeport, Conn.

Unlike prior art devices, which directly measure the amount of light remaining in a beam after impinging upon a fiber particle, this invention employs the characteristics of scattered light 8 as sensed by photodetector 10 and analyzed by dimension measuring circuit 11.

In operation, vacuum pump 4 is attached to one end of flow tube 5b, and draws fiber-laden air 16 through tubes 5a, 5b. The flow rate of air 16 is chosen such that the flow in tubes 5a, 5b is laminar in nature. Also, the lengths of tubes 5a, 5b are chosen such that there is a sufficient distance for the laminarly-flowing, fiber-laden air 16 to align the longitudinal axis of fiber 9 with the direction of the airflow. With reference also to FIG. 2, it is preferred that a small gap 15 be formed between tubes 5a, 5b to permit collimated beam 6 to pass therethrough. Gap 15 can be used as a beam-steering device to preferentially direct scattered light 8 having the preselected orientation to sensor 10.

In general, when fiber 9 enters the path of laser beam 6, light is scattered. If fiber 9 is aligned with the flow of air 16, then its longitudinal axis will be substantially perpendicular to laser beam 6 thus scattering light into a plane normal to the axis of tubes 5a and 5b (best seen in FIG. 1). The portion of scattered light 8 having this preselected orientation can be collected by lens assembly 13 and focused onto photodetector 10 producing a measuring signal 17, the characteristics of which are indicative of the dimensions of fiber 9.

Signal 17 can be processed by dimension measuring circuit 11, which can produce a perceptible representation of the dimensions of fiber 9. Responsive to scattered light 8, photodetector 10 generates a voltage, the duration of which is essentially a function of the length and velocity of fiber 9, and the thickness of beam 6. If the thickness of beam 6 and the velocity of fiber 9 are substantially fixed, the length of the fiber 9 can be determined by measuring, for example, the duration of signal 17.

The amplitude of signal 17 typically depends upon: (1) the wavelength of beam 6 and its intensity at the location of fiber 9; (2) the diameter of fiber 9; and (3) the angles over which scattered light 8 is collected. It is preferred that the wavelength of the light source and the light collection angles be fixed by the design of the system. It also is desirable to keep the intensity of beam 6 substantially constant in the region in which fibers 9 might be detected. Thus, the voltage amplitude of signal 17 can be made to depend primarily on the diameter of fiber 9.

For ease of analysis, it is desired that the dependency of the voltage amplitude of signal 17 upon fiber dimensions be both linear and monotonic. However, where linearity is difficult or impossible to achieve, dependency can nevertheless be determined by an approximately monotonic signal. This signal can be provided by collecting scattered light 8 over a preselected range of collection angles.

As an example, for a light wavelength of about 670 nm, it is preferred to collect light from about 600 to about 120° relative to the direction of laser beam 6, thus producing an approximately monotonic voltage amplitude range, which is indicative of the diameter of a small fiber 9 of less than about 10 microns or so. Furthermore, it is preferred that beam 6 from light source 7 be very thin to simplify the measurement of the length of fiber 9, although, even where the length of fiber 9 is generally less than the thickness of beam 6, fiber lengths can still be measured.

It is preferred that a laser diode be used as light source 7 because it typically produces an inherently thin, oval-shaped beam 6. It is preferred that light source 7 be oriented such that the wide dimension of beam 6 is generally perpendicular to the flow of air 16 and that fiber 9 passes through the thin dimension of beam 6. To further minimize the thickness of beam 6, a focusing lens 12, for example, a cylindrical lens, can be used. One advantage of cylindrical lens 12 is that the width of beam 6 is not operatively reduced thereby.

In general, the beam intensity across the width of beam 6 is approximately Gaussian. Therefore, it is preferred to place beam block 18, having aperture 14 therein, in the path of beam 6 to substantially block low-intensity edges of beam 6. Typically, Fresnel diffraction can occur from the edges of aperture 14. Although this diffraction can cause some ripple in the intensity across the width of the remaining beam 6, the "bright edge" associated with this diffraction helps to raise the intensity where the Gaussian intensity curve otherwise would be falling. Thus, the intensity across the width of beam 6 is nearly constant with some ripple.

As stated previously, existing prior art devices typically analyze the amount of light directly received from the light source, as affected by the passage of an airborne fiber through the light beam. The present invention preferably does not analyze direct light signals, but rather, scattered light signals having a preselected orientation after striking the fiber.

Figure 3:
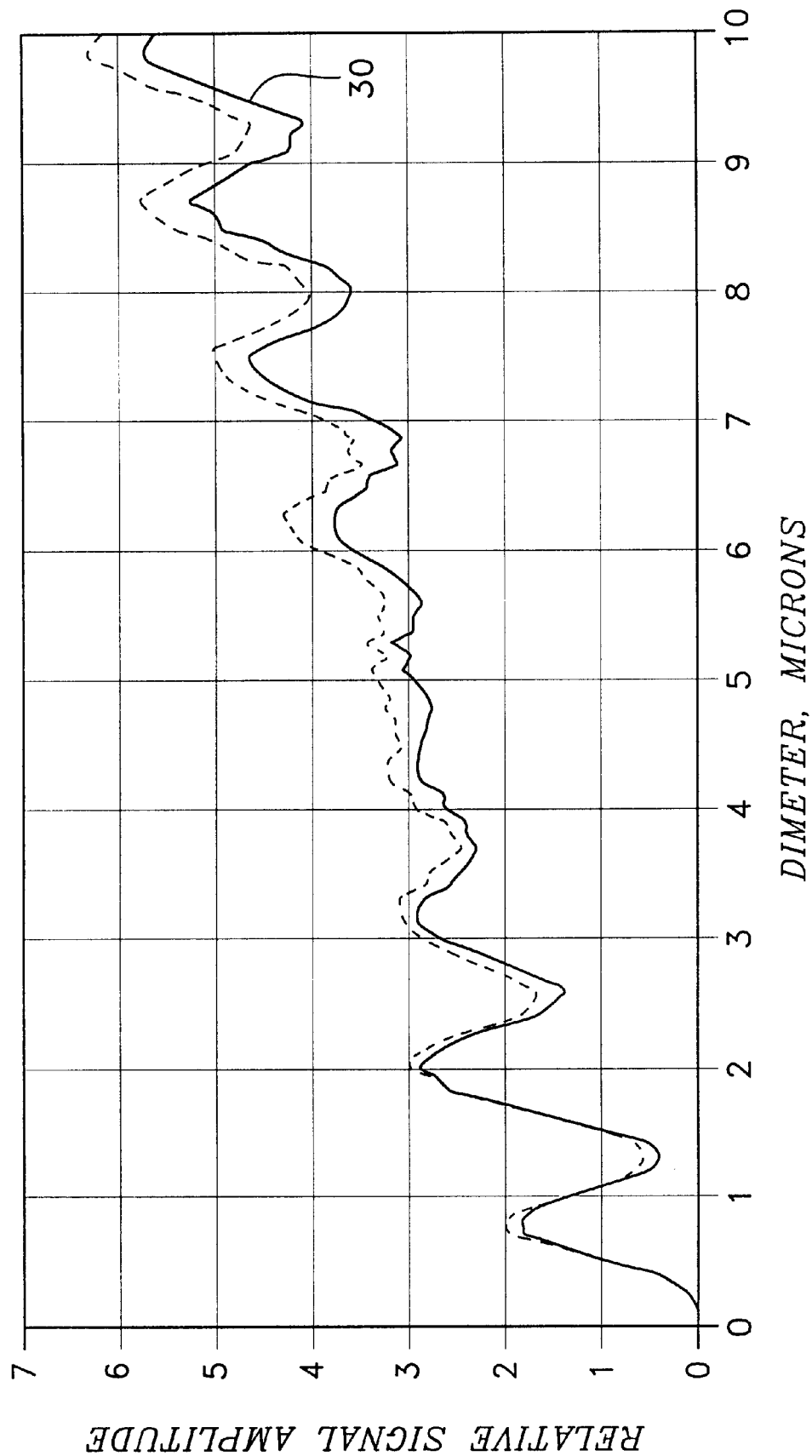
FIG. 3 is a graphical illustration of a light sensor amplitude vs. fiber diameter generated in response to detected forward scattered light.

The advantages of this approach can be better appreciated by examining the response of a photodetector to directly impinging light as a function of fiber diameter and the light beam being attenuated by fibers, as seen in FIG. 3. Response curve 30 arises from the direct impingement of a collimated light beam upon a photodetector as a function of fiber diameter. Response curve 30 is neither linear nor monotonic and may not reliably produce a signal that is representative of fiber diameter.

Figure 4:
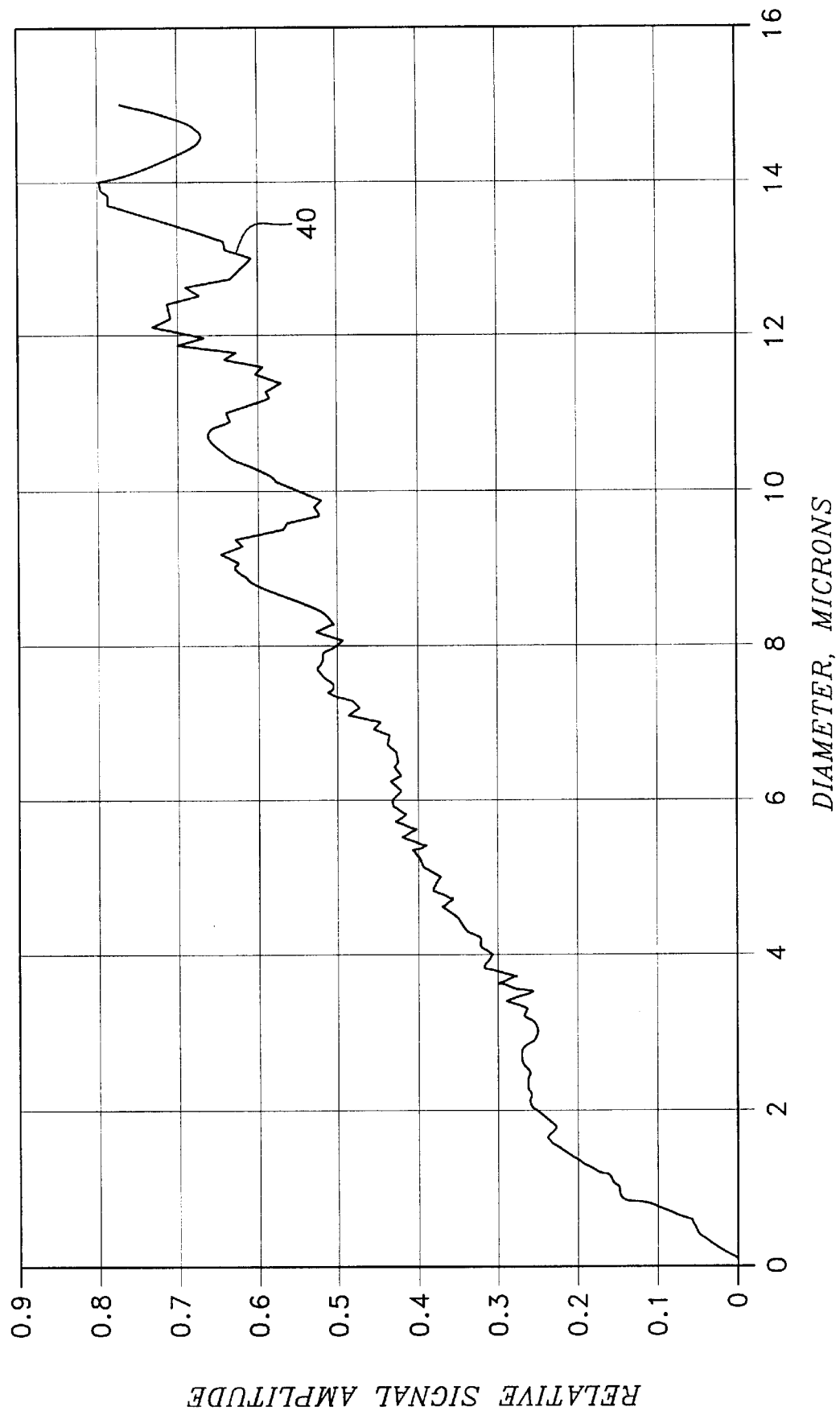
FIG. 4 is a graphical illustration of a light sensor amplitude vs. fiber diameter generated in response to light scattered laterally from the beam path at about 60° to 120°.

However, when scattered light 8 having a preselected orientation is used to determine fiber diameter, the photodetector response can be made approximately monotonic over a predetermined range, as seen with response curve 40 in FIG. 4. The approximate monotonicity of response curve 40 is associated with fiber sizes below about 8–10 microns, and especially below about 9 microns, using a light wavelength of about 670 nm. A skilled artisan would recognize that light at other wavelengths may be desirable for fibers of other diameters. In general, the shorter the light wavelength, the narrower the dimension of the fibers that can be accurately determined.

Two linear approximations can be applied over the monotonic range of curve 40 to better estimate the response. For example, one linear approximation can be employed for fiber diameters of up to about 2 microns and a second linear approximation may be used for fiber diameters between about 2 microns and about 8 microns.

In preferred embodiments of the present invention, the scattered light 8 sensed by light sensor 10 and its lens 13 are preferred to be at a preselected orientation of between about 60° and about 120° relative to the beam path.

All publications mentioned in this specification are indicative of the level of skill of the skilled in the art to which this invention pertains. All publications are herein incorporated by reference to the same extent as if each individual publication was specifically but individually indicated to be incorporated by reference.

While specific embodiments of practicing the invention have been described in detail, it will be appreciated by those skilled in that art that various modifications and alternatives to those details could be developed in light of the overall teachings of the disclosure. Indeed, a skilled artisan would recognize that, although the invention has been described in terms of determining the dimensions of airborne fibers, the apparatus and method illustrated in detail herein also can be used to detect, characterize, and visualize other types of particles having specific optical properties. Accordingly, the particular arrangements of the methods and apparatus disclosed are meant to be illustrative only and not limiting to the scope of the invention, which is to be given the full breadth of the following claims, and any and all embodiments thereof.

What is claimed is:

1. A device for measuring a dimension of a fiber in a fiber-containing air sample, comprising:
   a. flow means for providing a laminar flow to at least a portion of the fibers in said air sample;
   b. a light source for projecting a light beam along a beam path to impinge upon a non-oscillating first fiber in said laminar flow of fibers so as to become scattered light; and
   c. one and only one light detector for sensing a portion of the scattered light and not unscattered light from the light beam and for generating an output from which a dimension of said non-oscillating first fiber can be provided;

wherein the light detector generates a measured signal responsive to the portion of the scattered light it receives, a value of a property of said measured signal from said light detector being generally proportional to a fiber dimension.

2. The device of claim 1, wherein said flow means comprises a fiber separation device.

3. The device of claim 1 wherein the light source is a collimated laser beam.

4. The device of claim 3 wherein the light detector is a photodetector for providing a measuring signal having a signal amplitude responsive to a portion of the scattered light which it receives.

5. The device of claim 1 further comprising processing means for calculating said dimension of said first fiber from said measured signal.

6. The device of claim 5 wherein the measured signal has an amplitude and a duration, the amplitude being generally proportional to a fiber diameter and the duration being generally proportional to a fiber length.

7. The device of claim 4 wherein the measured signal is essentially monotonic with respect to fiber diameter.

8. The device of claim 1 wherein said sensed portion of scattered light has a preselected orientation relative to the beam path.

9. The device of claim 8 wherein the preselected orientation is between about 60 degrees and about 120 degrees relative to the beam path so as to better distinguish fibers of less than about 8–10 μm.

10. The device of claim 1 further comprising a lens for receiving a portion of the scattered light which is directed at about 60° to about 120° from said beam path, and for directing said received scattered light to said light detector.

11. A device for measuring a dimension of an airborne fiber in a fiber-containing air sample, comprising:
    a. flow means for providing a laminar flow to at least a portion of the fibers in said air sample;
    b. a collimated light source for projecting a light beam along a beam path to impinge upon a non-oscillating first fiber in said laminar flow so as to become scattered light thereby; and
    c. photodetector means comprising one and only one detector for sensing a portion of the scattered light and not unscattered light from the light beam and for providing an electrical output representative of a sensed scattered light, said electrical output being in the form of a signal, a value of a property of said signal provided by said one detector being generally proportional to a fiber dimension; and
    d. processing means for receiving said electrical output and for providing a perceptible indication of a dimension of said non-oscillating first fiber.

12. The device of claim 11 wherein the electrical output has an amplitude and a duration, the amplitude being generally proportional to a fiber diameter and the duration being generally proportional to a fiber length.

13. The device of claim 11 wherein said photodetector means is disposed at a preselected orientation relative to the beam path.

14. The device of claim 13 wherein said preselected orientation is between about 60 degrees and about 120 degrees relative to the beam path.

15. The device of claim 11 further comprising lens means for receiving said portion of said scattered light prior to directing it to said photodetector means.

16. A method for measuring a dimension of an airborne fiber, comprising the steps of:
    a. providing a fiber-containing air sample having a laminar flow;
    b. projecting a light beam along a beam path into said air sample, a portion of the light beam impinging upon a non-oscillating first fiber in said air sample and becoming scattered light thereby; and
    c. sensing a portion of the scattered light and not unscattered light from the light beam by one and only one light detector and producing an electrical output which is representative of a sensed portion of said scattered light, said electrical output being in the form of a signal, a value of a property of said signal from said one light detector being generally proportional to a fiber dimension; and
    d. processing said electrical output to produce a perceptible indication of a dimension of said non-oscillating first fiber.

17. The method of claim 16, further comprising the step of calculating the diameter of said first fiber from said measured signal.

18. The device of claim 17 wherein the measuring signal has an amplitude and a duration, said amplitude being generally proportional to a fiber diameter and said duration being generally proportional to a fiber length.

19. The method of claim 16 wherein said sensing step (c) measures scattered light having a preselected orientation relative to the beam path.

20. The method of claim 19 wherein the preselected orientation is between about 60 degrees and about 120 degrees relative to the beam path.

21. The method of claim 20 further including focusing a portion of said scattered light having said preselected orientation with an optical lens before said sensing step (c).

22. The method of claim 16 wherein the light beam is a collimated laser beam.

23. A device for measuring a dimension of a fiber in a fiber-containing air sample, comprising:
    a. flow means for providing a laminar flow to at least a portion of the fibers in said air sample, said portion of said fibers being substantially aligned with an airflow;
    b. a light source for projecting a light beam along a beam path to impinge upon a first fiber in said laminar flow of fibers so as to become scattered light, said first fiber being substantially aligned with an airflow; and c. one and only one light detector for sensing a portion of the scattered light and not unscattered light from the light beam and for generating an output from which a dimension of said first fiber can be provided;

wherein the light detector generates a measured signal responsive to the portion of the scattered light it receives, a value of a properly of said measured signal being generally proportional to a fiber dimension.

24. A device for measuring a dimension of an airborne fiber in a fiber-containing air sample, comprising:

a. flow means for providing a laminar flow to at least a portion of the fibers in said air sample, said portion of said fibers being substantially aligned with an airflow;

b. a collimated light source for projecting a light beam along a beam path to impinge upon a first fiber in said laminar flow, said first fiber being substantially aligned with the airflow, so as to become scattered light thereby; and c. photodetector means including one and only one light detector for sensing a portion of the scattered light and not unscattered light from the light beam and for providing an electrical output representative of a sensed scattered light, said electrical output being in the form of a signal, a value of a property of said signal from said light detector being generally proportional to a fiber dimension; and d. processing means for receiving said electrical output and for providing a perceptible indication of a dimension of said first fiber.

25. A method for measuring a dimension of an airborne fiber, comprising the steps of:

a. providing a fiber-containing air sample having a laminar flow;

b. projecting a light beam along a beam path into said air sample, a portion of the light beam impinging upon a first fiber in said air sample, said first fiber being substantially aligned with the flow of air in said air sample, and becoming scattered light thereby; and c. sensing using one and only one light detector a portion of the scattered light and not unscattered light from the light beam and producing an electrical output which is representative of a sensed portion of said scattered light, said electrical output being in the form of a signal, a value of a property of said signal from said light detector being generally proportional to a fiber dimension; and d. processing said electrical output to produce a perceptible indication of a dimension of said first fiber.

26. A device for measuring a dimension of a fiber in a fiber-containing air sample, comprising.

a. flow means for providing a laminar flow in a flow channel having a longitudinal axis, to at least a portion of the fibers in said air sample;

b. a light source for projecting a light beam along a beam path to impinge upon a first fiber in said laminar flow of fibers so as to become scattered light, said beam path being substantially normal to said longitudinal axis of said flow channel; and c. one and only one light detector for sensing a portion of the scattered light and not unscattered light from the light beam and for generating an output from which a dimension of said first fiber can be provided;

wherein the light detector generates a measured signal responsive to the portion of the scattered light it receives, a value of a property of said measured signal being generally proportional to a fiber dimension.

27. A device for measuring a dimension of an airborne fiber in a fiber-containing air sample, comprising:

a. flow means for providing a laminar flow in a flow channel having a longitudinal axis to at least a portion of the fibers in said air sample;

b. a collimated light source for projecting a light beam along a beam path to impinge upon a first fiber in said laminar flow, said beam path being substantially normal to said longitudinal axis of said flow channel, so as to become scattered light thereby; and c. photodetector means including one and only one light detector for sensing a portion of the scattered light and not unscattered light from the light beam and for providing an electrical output representative of a sensed scattered light, said electrical output being in the form of a signal, a value of a property of said signal from said light detector being generally proportional to a fiber dimension; and d. processing means for receiving said electrical output and for providing a perceptible indication of a dimension of said first fiber.

28. A method for measuring a dimension of an airborne fiber, comprising the steps of:

a. providing a fiber-containing air sample having a laminar flow in a flow channel having a longitudinal axis;

b. projecting a light beam along a beam path into said air sample, a portion of the light beam impinging upon a first fiber in said air sample, said beam path being substantially normal to said longitudinal axis of said flow channel, and becoming scattered light thereby; and c. sensing using one and only one light detector a portion of the scattered light and producing an electrical output which is representative of a sensed portion of said scattered light and not unscattered light from the light beam, said electrical output being in the form of a signal, a value of a property of said signal being generally proportional to a fiber dimension; and d. processing said electrical output to produce a perceptible indication of a dimension of said first fiber.

* * * * *